(12) United States Patent
Rapaport

(10) Patent No.: US 7,879,814 B2
(45) Date of Patent: Feb. 1, 2011

(54) METHODS AND THERAPEUTIC COMPOSITIONS IN THE TREATMENT OF ADVANCED CANCER

(76) Inventor: Eliezer Rapaport, 14 Prentiss La., Belmont, MA (US) 02178

( * ) Notice: Subject to any disclaimer, the term of this patent is extended or adjusted under 35 U.S.C. 154(b) by 1313 days.

(21) Appl. No.: 10/953,084

(22) Filed: Sep. 30, 2004

(65) Prior Publication Data

US 2005/0079225 A1 Apr. 14, 2005

Related U.S. Application Data

(63) Continuation of application No. PCT/US03/01166, filed on Jan. 16, 2003.

(51) Int. Cl.
*A01N 43/04* (2006.01)
*A61K 31/70* (2006.01)

(52) U.S. Cl. .................................................. 514/47
(58) Field of Classification Search ............... None
See application file for complete search history.

(56) References Cited

U.S. PATENT DOCUMENTS

| | | | |
|---|---|---|---|
| 4,880,918 A | 11/1989 | Rapaport | |
| 5,049,372 A * | 9/1991 | Rapaport | 424/1.77 |
| 5,415,873 A | 5/1995 | Trepel et al. | |
| 5,641,500 A | 6/1997 | Trepel et al. | |
| 6,828,346 B2 * | 12/2004 | Joshi-Hangal et al. | 514/449 |
| 7,148,210 B2 * | 12/2006 | Abraham | 514/79 |

FOREIGN PATENT DOCUMENTS

CA 2 151 826 5/1995

OTHER PUBLICATIONS

Vinciguerra, "A comparative assessment of home versus hospital comprehensive treatment for advanced cancer patients", Journal of Clinical Oncology, vol. 4, 1986, abstract.*
Brook et al., "Use of ATP-MgCl2 in the evaluation and treatment of children with pulmonary hypertension secondary to congenital heart defects", Circulation, vol. 90, No. 3, 1994, pp. 1287-1293.*
Hatta et al: "Cytotoxic effect of extracellular AIP on L1210 leukemic and normal hemopoietic stem cells" Leukemia Research, New York, NY, US, vol. 18, No. 8, pp. 637-641, Aug. 1, 1994.
Batra et al.: "Release of intracellular calcium and stimulation of cell growth by AIP and histamine in human ovarian cancer cells (SKOV—3)" Cancer Letters, New York, NY, US, vol. 77, No. 1, pp. 57-63, Feb. 28, 1994.
Vandewalle et al.: "Effect of extacellular ATP on breast tumor cell growth, implication of intracellular calcium" Cancer Letters, New York, NY, US, vol. 85, No. 1, pp. 47-54, Sep. 30, 1994.
Supplementary European Search Report issued Aug. 6, 2009, during the prosecution of European Application No. 03715933.2—1216 / 1583543.

* cited by examiner

*Primary Examiner*—Traviss C McIntosh, III
(74) *Attorney, Agent, or Firm*—Connolly Bove Lodge & Hutz LLP

(57) ABSTRACT

Adenine nucleotides such as adenosine 5'-monophosphate (AMP), adenosine 5'-diphosphate (ADP) or adenosine 5'-triphosphate (ATP) and/or adenosine and inorganic phosphate are administered in the treatment of advanced cancer in an out-patient setting and without serious side effects. Administration of up to 100 micrograms/kilogram/minute of continuous intravenous infusions of ATP for 8-10 hours, can be performed on an out-patient basis to patients who do not otherwise require hospitalization. No serious side effects, defined as grades 3 or 4 toxicity are observed during such an infusion.

11 Claims, No Drawings

METHODS AND THERAPEUTIC COMPOSITIONS IN THE TREATMENT OF ADVANCED CANCER

CROSS-REFERENCE TO RELATED APPLICATION

This application is a continuation of International Application No. PCT/US03/01166 filed Jan. 16, 2003, the entire disclosure of which is incorporated herein by reference.

TECHNICAL FIELD

The present invention relates to methods and therapeutic compositions that improve the treatment of advanced cancer by continuous intravenous infusions of adenine nucleotides such as adenosine 5'-monophosphate (AMP), adenosine 5'-diphosphate (ADP) or adenosine 5'-triphosphate (ATP) and/or adenosine and inorganic phosphate by virtue of the administration being performable on an out-patient basis and without serious (grades 3 and 4 toxicity) side effects.

BACKGROUND ART

The treatment of cancer by administration of ATP has been disclosed in two U.S. patents and their European and Japanese counterparts. U.S. Pat. No. 4,880,918 and European patent No. 0 100 022 to Rapaport teach and disclose the anti-tumor activities of ATP. These patents outline methods for the killing of human tumors by exposing them to ATP for periods of at least 48 hours (see column 3 lines 41, 45 and 51, column 5 line 37, column 6 lines 23, 25 and 45, column 7 line 48, column 9 line 9, and claim number 3 of U.S. Pat. No. 4,880,918). European patent 0 100 022 contains similar disclosure. U.S. Pat. No. 5,049,372 and its parallel European patent No. 0 352 477 B1 to Rapaport teach and disclose the administration of ATP in the treatment of cancer cachexia and inhibition of weight loss resulting from cancer cachexia. Based on the teachings of these patents and after the issue of these patents, the administration of ATP in the treatment of advanced, non-resectable cancers was utilized in human clinical trials.

Three clinical trials have examined the effects of continuous intravenous infusions of ATP in advanced cancer patients (Haskell et al., Phase I trial of extracellular adenosine 5'-triphosphate in patients with advanced cancer. Medicinal and Pediatric Oncology 1996; 27(3):165-173; Mendoza et al., Adenosine triphosphate (ATP) for advanced non-small cell lung cancer (NSCLC): A Phase II multicenter study. Proceedings Amer Soc Clin Oncology 1996; 15:A1238; Haskell et al., Phase II study of intravenous adenosine 5'-triphosphate in patients with previously untreated stage IIIB and Stage IV non-small cell lung cancer. Invest New Drugs 1998; 16(1): 81-85; Agteresch et al., Randomized Clinical Trial of adenosine 5'-triphosphate in patients with advanced non-small-cell lung cancer. J Natl Cancer Inst 2000; 92(4):321-328; Agteresch, Dagnelie et al., Pharmacokinetics of intravenous ATP in cancer patients. Eur J Clin Pharmacol 2000; 56:49-55.). The published results of these trials provide information about the toxicity, pharmacokinetics, anticachectic and antitumor actions of ATP.

Study One: Haskell et al., (1996, supra). In the initial Phase I/II clinical trial, ATP was administered as a continuous intravenous infusion for 96 hr, once every 4 weeks, at rates of 50, 75 or 100 mcg/kg/min (Haskell et al., 1996, supra). The trial included 14 men with advanced, non-resectable cancer, eight of whom suffered from stage IIIB/IV non-small cell lung cancer. Most of the patients were chemotherapy-naïve. One patient received one infusion; 4 received 2 infusions; 6 received 3 infusions; 1 received 4 infusions; and 2 received 6 infusions.

The dose-limiting toxicity seen in this study was a cardiopulmonary reaction characterized by tightness of the chest and dyspnea that resolved shortly after discontinuing the ATP infusion. This reaction was seen in all three patients (100%) infused at 100 mcg/kg/min; in 3 of 6 (50%) patients infused at 75 mcg/kg/min; and, in 4 of 11 patients (36%) who received 50 μg/kg/min. In some cases, this reaction was accompanied by electrocardiographic changes suggestive of myocardial ischemia. Less frequent or less prominent adverse effects that may, or may not, have been related to ATP treatment were injection site reactions ("local reactions," pain and phlebitis), hypoxia, hypotension, ECG abnormalities, nausea and/or emesis, abdominal pain, dizziness, headache, anxiety, back or neck pain, anemia, and leukopenia. In summary, 21% of all adverse events recorded in this phase I/II trial were grade 3 or 4 (defined as severe or life-threatening). These included 6 events of dyspnea, 2 events of hypoxia, 5 events of chest pain, 1 event of hypotension, 2 events of nausia/emesis, 1 event of dizziness, 1 event of grade 3 headache and one event of grade 3 anxiety. 79% of all adverse events recorded were of grade 1 or 2 (defined as mild or moderate). Patients required hospitalization for at least 4 days once every four weeks for the purpose of the monitored ATP administration.

With respect to the pharmacokinetic properties of ATP, Haskell et al., (1996, supra) measured the whole blood concentrations of ATP of 18 subjects before and at 24, 48, 72, and 96 hours during and after infusions at rates of 50, 75, or 100 mcg/kg/min. The ATP concentrations were found to vary widely but in general, they increased 30%-40% after 4 hours and the highest blood concentrations were seen at 24 hours of infusion. These concentrations averaged 63%, 67%, and 113%, respectively, higher than the pretreatment values of blood ATP levels. The blood concentrations of ATP were relatively constant or slightly declined during the interval between 24 and 96 hours of the infusion. Little data are available concerning the decay of ATP concentrations post-infusion.

These authors concluded that prolonged infusions of ATP are feasible with acceptable toxicity and that 50 mcg/kg/min is both the maximum tolerated dose and the most appropriate dose rate for subsequent Phase II testing of 96-hours infusions of ATP in patients with advanced cancers.

Study Two: Mendoza et al., (1996, supra), and Haskell et al., (1998, supra). The second human clinical trial conducted by Mendoza et al., (1966, supra), and Haskell et al., (1998, supra), was a Phase II multicenter study of 15 chemotherapy-naïve, stage IIIB/IV non-small cell lung cancer patients. These patients were continuously infused at rates of 50 or 65 mcg/kg/min of ATP for 96 hours, once every 4 weeks (Mendoza et al., 1996, supra; Haskell et al., 1998, supra). Two patients received 1 infusion; 8 received 2 infusions; 4 received 4 infusions; and 1 received 7 infusions.

A large proportion of the patients in this study experienced a variety of adverse effects, including chest pain, dyspnea, coughing, anxiety, injection site pain, chest tightness, headache, insomnia, and hot flashes. Almost one-half of the patients exhibited abnormal electrocardiograms. In some patients, there were minor reductions in hematocrit, hemoglobin, total protein, albumin, sodium, and calcium and minor increases in serum glucose. No significant hematologic, renal, hepatic, or gastrointestinal toxicity was noted. Six patients reported severe (grade 3) adverse effects and two patients had life-threatening (grade 4) dyspnea. All patients were hospitalized for at least 4 days during each of the monitored 96 hours infusion cycles.

Although no significant tumor shrinking was observed, the majority of patients exhibited stable disease after treatment with ATP. In addition, beneficial effects were seen on weight gain, performance status, and the overall survival of patients with non-small cell lung cancer.

Study Three: Agteresch et al., (2000, supra) and Agteresch, Dagnelie et al., (2000, supra). The third trial was a randomized, open label Phase III study of 52 assessable, previously treated, refractory, stage IIIB/IV non-small cell lung cancer patients who failed previous chemotherapy and/or radiation therapy. The patients were randomized into two groups. One group of 25 patients received best supportive care and infusions of ATP while the other group of 27 patients received only best supportive care. The ATP-treated patients received ten 30-hours infusions, the first seven at 2-week intervals and the last three at 4-week intervals. In each case, the infusion was started at 20 mcg/kg/min and increased every 30 min by mcg/kg/min until adverse effects developed or a maximum dose of 75 mcg/kg/min was reached. If adverse effects developed, the dose was reduced stepwise until the adverse effects disappeared. Eleven patients received 1-3 infusions; five received 4-6 infusions; and 12 received 7-10 infusions of ATP.

The adverse experiences seen during treatment were generally mild or moderate and consisted of chest discomfort, urge to take a deep breath, flushing, nausea, lightheadedness, headache, sweating, anxiety, and palpitations. More pronounced side effects were injection site reactions and dyspnea. In patients with chest discomfort, electrocardiograms did not exhibit changes suggestive of myocardial ischemia. All side effects resolved within minutes of lowering the rate of ATP infusion. Of all adverse events recorded in this trial, 81 were of grade 1 (mild), 5 of grade 2 (moderate), none of grade 3 (severe) and 5 were of grade 4 (life threatening). Patients were hospitalized for 1 or 2 days during the monitored infusions of ATP, which were administered at 2 or 4 weeks intervals.

In this study, ATP administration was associated with beneficial effects on body weight and voluntary muscle strength and with improvements in Quality of Life domains. Thus, the authors concluded that ATP shows promise as an agent for the palliation of cancer cachexia.

It is therefore concluded that all prior art related to issued patents and detailed publications of three human clinical trials, established a particular protocol of ATP administration in advanced cancer patients. Such a protocol includes continuous intravenous infusions of ATP for periods longer than 24 hours during which time the patient is being hospitalized. The continuous infusions are administered for multiple treatment cycles every 2-4 weeks. During these infusion protocols some grades 3 and 4 (severe and life threatening) toxicity have been recorded.

SUMMARY OF THE INVENTION

The present invention discloses for the first time a method for treating advanced cancer in an out-patient setting by administration of adenine nucleotides such as adenosine 5'-monophosphate (AMP), adenosine 5'-diphosphate (ADP) or adenosine 5'-triphosphate (ATP) and/or adenosine and inorganic phosphate to a human host.

In particular, the present invention is concerned with a method for treating advanced cancer in an out-patient setting, by administering to a human host in need thereof a member selected from the group consisting of: (a) a mixture of adenosine and inorganic phosphate; and (b) an adenine nucleotide wherein said adenine nucleotide containing adenosine moiety(ies) and phosphate moiety(ies) and undergoes rapid degradation to adenosine and inorganic phosphate after administration to said host. Such an adenine nucleotide can be, but is not limited to, AMP, ADP or ATP. In a preferred aspect, the present invention relates to using ATP in the treatment of advanced cancer in an out-patient setting.

It is highly desirable and in the public interest to invent methods and pharmaceutical compositions, which would enable advanced cancer patients to: 1. Receive continuous intravenous infusions of ATP in an out-patient setting for a period of up to about 10 hours, and preferably about 8 to about 10 hours of each cycle. 2. Receive continuous intravenous infusions of ATP with no grades 3 or 4 toxicity or adverse events.

Such methods and pharmaceutical compositions of ATP administration in the treatment of advanced cancer would minimize expense and discomfort to the patients, resulting in much wider acceptance of ATP treatment protocols.

These objectives where accomplished by the present invention of methods and pharmaceutical compositions for ATP in the treatment of advanced, non-resectable cancer. In a preferred embodiment, continuous intravenous infusions of ATP at a maximum rate of 100 mcg/kg/min are administered. Infusions are administered in an infusional center on an out-patient basis. Infusions can also be administered at the patient's home on a home care basis or in a clinic. Infusions are provided continuously for about 8 hours, once or more weekly. A minimum of 8 weekly cycles is administered. During the treatment period and in order to assess the patient's response to the ATP treatment, a number of parameters believed to reflect Quality of Life (QoL), cancer cachexia and tumor progression are monitored. These include, tumor status (by imaging), body weight, QoL evaluation (e.g. EORTC questionnaire), skeletal muscle strength, Karnofsky Performance Status as well as survival.

DETAILED DESCRIPTION OF THE INVENTION

It has been found pursuant to the present invention that a host suffering from advanced cancer can be treated by being administered a member selected from the group consisting of: (a) a mixture of adenosine and inorganic phosphate; and (b) an adenine nucleotide wherein said adenine nucleotide containing adenosine moiety(ies) and phosphate moiety(ies) and undergoes rapid degradation to adenosine and inorganic phosphate after administration to said host.

Examples of such materials are adenosine 5'-monophosphate (AMP), adenosine 5'-diphosphate (ADP), adenosine 5'triphosphate (ATP) and/or mixtures of adenosine and an inorganic phosphate. In addition, pharmaceutically acceptable salts, or metal complexes, or chelates, or liposomes, or radio-nuclides of the above compounds can be used.

Preparations containing the above ingredients can be employed in a variety of conventional pharmaceutical preparations. These preparations can contain organic or inorganic material suitable for internal administration. The high solubility of AMP and/or ADP and/or ATP salts and/or adenosine and phosphate salts in isotonic aqueous solutions of sodium chloride enable administration of these agents in the form of injection or infusion of single or multiple doses. The injection or infusion can be intraperitoneal, intravenous, or intra-arterial. AMP and/or ADP and/or ATP and/or adenosine and phosphate salts are also suitable for oral, enteral, or topical application when employed with conventional organic or inorganic carrier substances.

The effective doses are in the range of about 1-500 mg/kg of body weight per 24 hours for oral or topical administration, and 0.1-100 mg/kg of body weight per 24 hours for injections. Continuous intravenous, intraperitoneal, or intraarterial infusions of AMP and/or ADP and/or ATP and/or adenosine and phosphate salts in a suitable salt form is preferably administered at a rate of about 10-150 micrograms/kg of body weight per minute. The delivery of these agents can be performed using a variety of drug delivery systems including, but not limited to, pumps or liposomes.

The novel and unexpected discovery that ATP administrations in the treatment of advanced cancer can be performed on an out-patient basis and without serious (grades 3 or 4) side effects constitute the basis for the present invention. It means that it will now be possible to save patients and payers time and expense by avoiding hospitalization, while improving the advanced cancer patient's Quality of Life.

The invention is non-obvious since all prior art advocated continuous ATP infusions of longer than 24-48 hours in advanced cancer patients. The length of the continuous infusions, which was deemed essential for obtaining clinical efficacy, required hospitalization during the monitored infusions and resulted in some grades 3 or 4 toxicity. The unexpected nature of this invention is due to the surprising discovery that short (8 hours), weekly, continuous infusions of ATP, at rates even somewhat higher than what has been previously reported (Haskell et al., 1996, supra; Mendoza et al., 1996, supra; Haskell et al., 1998, supra; Agteresch et al., 2000, supra, and Agteresch, Dagnelie et al., 2000, supra), resulted in similar clinical efficacies with significantly reduced profiles of adverse effects. Thus, weekly continuous intravenous infusions of up to 100 mcg/kg/min of ATP in an out-patient setting, produced no grades 3 or 4 toxicity with clinical efficacy similar to what has been reported with utilization of the longer (30-96 hours) and less frequent (once every 2-4 weeks) infusion schedules.

Drug Formulation, Availability and Preparation Structure:

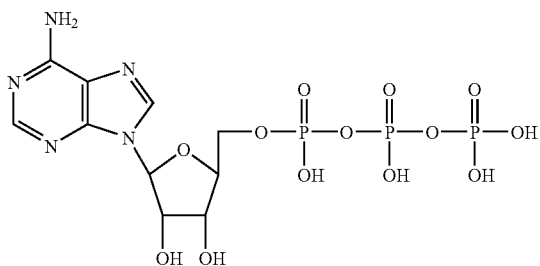

Adenosine 5'-triphosphate (ATP) is provided as a sterile solution in single use vials. Each vial contains 2 grams of ATP as a sodium salt in 20 ml of Water for Injection, at pH 6.8-7.2. The concentration of ATP is 100 mg/ml. Storage of the clinical solutions is at controlled refrigerated temperature (2-8° C.). Preparation of the infusion solution requires that the volume of one vial of ATP be aseptically removed using a syringe and added to a 250 ml bag of 0.5 N saline. The concentration of the final sterile solution is 8 mg/ml and is administered by continuous intravenous infusions using an Ivac or similar infusion device through venous access in a peripheral vein. If venous access is a problem, either a Hickman catheter or its equivalent or an Infusaport or its equivalent, are inserted to provide vascular access. ATP administration is performed as a slow intravenous infusion, in a hospital outpatient infusion center or at the patient's home or at an out-patient clinic, supervised by home care nursing expertise. All follow-up care is administered in hospital outpatient department or at the patient's home or clinic.

Experimental Protocol: Safety, Tolerability and Clinical Efficacy

Clinical Study Information:

Title of the Study: "A Phase I Study of the Safety and Pharmacokinetics of Adenosine 5'-Triphosphate (ATP) When Administered by Intravenous Infusion on a Multiple Weekly Dose Schedule to Patients with Advanced Malignancies (Solid Tumors)".

Protocol Number: DMS #D0005, IND # 60,517

The primary purpose of this study is to evaluate the safety, tolerability and pharmacokinetic properties of adenosine 5'-triphosphate (ATP) administered by continuous intravenous infusion to patients with histologically proven advanced treatment-resistant malignancies. The two secondary objectives of the study are to evaluate parameters that reflect quality of life and cancer cachexia in order to monitor any potential beneficial effects of ATP infusion in this patient population. Nine qualified patients have been enrolled in the study as of Jan. 1, 2002; seven of which received the first 3 cycles of the study drug and are therefore evaluable for the primary endpoints. Two of the seven evaluable patients had advanced prostate cancer with bone metastases and one each had advanced mesothelioma, metastatic breast cancer, metastatic melanoma, metastatic colon cancer and renal cell carcinoma.

| Patient | Age | Gender | Cancer Type | Status |
|---|---|---|---|---|
| 501 | 48 | Male | Metastatic colon cancer | Withdrawn: progressive disease-N.E. |
| 502 | 54 | Male | Metastatic mesothelioma | Completed Study-Evaluable |
| 503 | 75 | Male | Metastatic prostate cancer | Completed Study-Evaluable |
| 504 | 77 | Female | Metastatic breast cancer | Completed Study Evaluable |
| 505 | 63 | Female | Metastatic melanoma to scalp | Completed Study-Evaluable |
| 506 | 38 | Female | Metastatic colon cancer | Completed 6 cycles-Evaluable |
| 507 | 69 | Male | Metastatic prostate cancer | Completed Study-Evaluable |
| 508 | 65 | Male | Prostate cancer | Withdrawn: Opted not to continue-N.E. |
| 509 | 48 | Female | Renal cell carcinoma | Completed Study-Evaluable |

*N.E. = not evaluable

Overall, patients tolerated the ATP infusion well, with seven of nine patients tolerating the maximum allowable dose of 100 mcg/kg/min administered as a continuous 8 hours intravenous infusion once weekly for eight weeks.

| | Dose administered in µg/kg/min over 8 hour infusion | | | | | | | |
|---|---|---|---|---|---|---|---|---|
| Patient | Cycle 1 | Cycle 2 | Cycle 3 | Cycle 4 | Cycle 5 | Cycle 6 | Cycle 7 | Cycle 8 |
| 501 | 50 | 75 | Nd | Nd | nd | nd | nd | Nd |
| 502 | 50 | 75 | 100 | 100 | 100 | 100 | 100 | 100 |
| 503 | 50 | 75 | 100 | 100 | 100 | 100 | 100 | 100 |
| 504 | 50 | 75 | 100 | 100 | 100 | 100 | 100 | 100 |
| 505 | 50 | 75 | 100 | 100 | 100 | 100 | 100 | 100 |
| 506 | 50 | 75 | 100 | 100 | 100 | 100 | nd | Nd |
| 507 | 50 | 75 | 100 | 100 | 100 | 100 | 100 | 100 |
| 508 | 50 | nd | Nd | Nd | nd | nd | nd | Nd |
| 509 | 50 | 75 | 100 | 100 | 100 | 100 | 100 | 100 |

*nd = not done

No grade 2 cardiac ischemia or grades 3 or 4 toxicity have been observed. Several patients have subjectively commented on improved appetite and energy during the study.

SUMMARY OF DATA

Overall, the nine qualified patients tolerated the ATP infusion well. The seven evaluable patients tolerated the maximum allowable dose of 100 mcg/kg/min, administered as a continuous 8 hour intravenous infusion once weekly for eight weeks.

No grade 2 cardiac ischemia or grades 3 or 4 toxicity have been observed.

Several patients have subjectively commented on improved appetite and energy during the study.

It has been seen in patient 506 that ATP is well tolerated in terminal patients.

Increases in Global Health Status of the QOL EORTC QLQ-C30 from screening (week <1) to follow-up (week 10) with a decline at week 13 follow-up.

Decreases in appetite loss for all patients from screening to week 10 (follow-up) with a return to screening baseline at week 13 follow-up.

Consistent decreases in SGOT (serum glutamate oxaloacetate transaminase), SGPT (serum glutamate pyruvate transaminase) and serum LDH (lactate dehydrogenase) for all patients from week 1 (pre-dose) to week 13 (follow-up).

Stabilization of body weight from week 1 pre-dose to week 13 follow-up.

Small increases in Kamofsky Performance Status from week 1 pre-dose to week 13 follow-up.

Small increases in Skeletal Muscle Strength (voluntary) from screening (week <1) to week 8 (last infusion cycle).

The pharmacokinetics of ATP performed on weeks (cycles) 1, 3 and 8 demonstrated the following:

Increases in total blood ATP pools (red blood cell pools) from time 0 to 8 hours (end of the infusions) of about 70-90% with a decline to baseline (time 0) at 24 hours.

The average increases in Initial ATP Release Rates (from Red Blood Cells) from time 0 to 8 hours were about 200-400% with comparable increases in extracellular (blood plasma) ATP pools.

The foregoing establishes that ATP administered according to the present invention is safe and effective in the treatment of advanced cancer. Treatment of advanced cancer patients with ATP on an out-patient basis or home care basis, utilizing a treatment protocol that does not lead to grades 3 or 4 toxicity, will enhance the acceptability of such treatment among patients, physicians and insurers.

According to the above disclosure and teaching, variations of the present invention are possible. It is therefore understood that the present invention may be practiced in ways other than specifically described. Having thus described my invention, what I claim as new and useful and desire to secure by Letters Patent is:

REFERENCES

U.S. Patent documents
4,880,918, November 1989, Rapaport, Arrest and killing of tumor cells by adenosine 5'-diphosphate and adenosine 5'-triphosphate.
5,049,372, September 1991, Rapaport, Anticancer activities in a host by increasing blood and plasma adenosine 5'-triphosphate (ATP) levels.

Foreign Patent Documents
0100022, February 1984, Rapaport, Pharmaceutical compositions containing adenosine derivatives for use in treating tumours. European Patent Office.
0352477B1, January 1990, Rapaport, Use of adenosine 5'-phosphat in the treatment of cancer cachexia. European Patent Office.

Published Articles
Agteresch H, Dagnelie P, van der Gaast A, Stijnen T, and Wilson J H P. Randomized Clinical Trial of adenosine 5'-triphosphate in patients with advanced non-small-cell lung cancer. J Natl Cancer Inst 2000; 92(4):321-328.
Agteresch H, Dagnelie P C, Rietveld T, van den Berg J W O, Danser A H J, and Wilson J H P. Pharmacokinetics of intravenous ATP in cancer patients. Eur J Clin Pharmacol 2000; 56:49-55.
Haskell C M, Mendoza E, Pisters K M, Fossella F V, and Figlin R A. Phase II study of intravenous adenosine 5'-triphosphate in patients with previously untreated stage IIIB and Stage IV non-small cell lung cancer. Invest New Drugs 1998; 16(1):81-85.
Haskell C M, Wong M, Williams A, and Lee L Y. Phase I trial of extracellular adenosine 5'-triphosphate in patients with advanced cancer. Medicinal and Pediatric Oncology 1996; 27(3):165-173.
Mendoza E, Fosella F, Haskell C, Pisters K, Orlandi C, Dixon M, and Figlin R. Adenosine triphosphate (ATP) for advanced non-small cell lung cancer (NSCLC): A Phase II multicenter study. Proceedings Amer Soc Clin Oncology 1996; 15:A1238.

The invention claimed is:

1. A method for treating advanced, non-resectable cancer by administering to a human patient in need thereof in an out-patient setting an effective amount of a member selected from the group consisting of a mixture of adenosine and inorganic phosphate; adenosine 5'-monophosphate (AMP); adenosine 5'-diphosphate (ADP); adenosine 5'-triphosphate (ATP);
- a pharmaceutically acceptable salt of the mixture of adenosine and inorganic phosphate; a chelate of the mixture of adenosine and inorganic phosphate; a metal complex of the mixture of adenosine and inorganic phosphate; a liposome of the mixture of adenosine and inorganic phosphate;
- a pharmaceutically acceptable salt of adenosine 5'-monophosphate (AMP); a chelate of adenosine 5'-monophosphate (AMP); a metal complex of adenosine 5'-monophosphate (AMP); a liposome of adenosine 5'-monophosphate (AMP);
- a pharmaceutically acceptable salt of adenosine 5'-diphosphate (ADP); a chelate of adenosine 5'-diphosphate (ADP); a metal complex of adenosine 5'-diphosphate (ADP); a liposome of adenosine 5'-diphosphate (ADP);
- a pharmaceutically acceptable salt of adenosine 5'-triphosphate (ATP); a chelate of adenosine 5'-triphosphate (ATP); a metal complex of adenosine 5'-triphosphate (ATP); and a liposome of adenosine 5'-triphosphate (ATP); or
- a mixture thereof.

2. The method of claim 1 wherein adenosine 5'-monophosphate (AMP) is administered to said patient.

3. The method of claim 1 wherein adenosine 5'-triphosphate (ATP) is administered to said patient.

4. The method of claim 3 wherein adenosine 5'-triphosphate is administered on a home care basis.

5. The method of claim 3 wherein adenosine 5'-triphosphate is administered in a clinic.

6. The method of claim 1 wherein said patient is suffering from solid tumors or leukemias.

7. The method of claim 1, wherein said administration is by injection in amounts of 0.1-1 milligrams per kilogram of body weight per 24 hours.

8. The method of claim 3 wherein the amount of adenosine 5'-triphosphate is about 10-150 micrograms per kilogram of body weight per minute and said administering is by infusion.

9. The method of claim 3 wherein the amount of adenosine 5'-triphosphate is about 0.1-100 milligrams per kilogram of body weight per 24 hours and said administering is by injections.

10. The method of claim 3 wherein the amount of adenosine 5'-triphosphate is about 1-500 milligrams per kilogram of body weight per 24 hours and administering is oral or topical.

11. The method of claim 1 wherein the mixture of adenosine and phosphate is administered to said patient.

* * * * *